United States Patent
Cole et al.

(10) Patent No.: US 8,968,465 B2
(45) Date of Patent: *Mar. 3, 2015

(54) BONE GRAFT SUBSTITUTE COMPOSITION

(71) Applicant: Wright Medical Technology, Inc., Memphis, TN (US)

(72) Inventors: Jantzen Cole, Cordova, TN (US); Timothy Smith, Middleton, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/156,850

(22) Filed: Jan. 16, 2014

(65) Prior Publication Data

US 2014/0134227 A1    May 15, 2014

Related U.S. Application Data

(63) Continuation of application No. 11/739,416, filed on Apr. 24, 2007, now Pat. No. 8,657,952, which is a continuation of application No. 10/402,192, filed on Mar. 28, 2003, now Pat. No. 7,211,266.

(60) Provisional application No. 60/368,924, filed on Mar. 29, 2002.

(51) Int. Cl.
| | |
|---|---|
| C04B 9/04 | (2006.01) |
| A61L 27/02 | (2006.01) |
| A61K 33/06 | (2006.01) |
| A61L 24/00 | (2006.01) |
| A61L 24/02 | (2006.01) |
| A61L 27/50 | (2006.01) |
| A61L 27/54 | (2006.01) |
| A61L 27/58 | (2006.01) |

(52) U.S. Cl.
CPC ............. *A61L 27/025* (2013.01); *A61K 33/06* (2013.01); *A61L 24/001* (2013.01); *A61L 24/02* (2013.01); *A61L 27/505* (2013.01); *A61L 27/54* (2013.01); *A61L 27/58* (2013.01); *A61L 2400/06* (2013.01); *A61L 2430/02* (2013.01)
USPC ........... 106/772; 424/696; 424/400; 423/530; 423/541.1; 423/548

(58) Field of Classification Search
None
See application file for complete search history.

(56) References Cited

U.S. PATENT DOCUMENTS

| | | |
|---|---|---|
| 3,573,947 A | 4/1971 | Kinkade et al. |
| 3,947,285 A | 3/1976 | Jones et al. |
| 4,430,760 A | 2/1984 | Smestad |
| 4,526,619 A | 7/1985 | Ohi et al. |
| 4,568,536 A | 2/1986 | Kronenthal et al. |
| 4,595,713 A | 6/1986 | St. John |
| 4,596,574 A | 6/1986 | Urist |
| 4,612,009 A | 9/1986 | Drobnik et al. |
| 4,619,655 A | 10/1986 | Hanker et al. |
| 4,650,665 A | 3/1987 | Kronenthal et al. |
| 4,681,763 A | 7/1987 | Nathanson et al. |
| 4,820,306 A | 4/1989 | Gorman et al. |
| 4,880,660 A | 11/1989 | Aasen et al. |
| 4,882,149 A | 11/1989 | Spector |
| 4,892,734 A | 1/1990 | Leonard |
| 4,975,526 A | 12/1990 | Kuberasampath et al. |
| 4,994,030 A | 2/1991 | Glowczewskie, Jr. et al. |
| 4,994,264 A | 2/1991 | Verdon et al. |
| 5,061,286 A | 10/1991 | Lyle |
| 5,073,373 A | 12/1991 | O'Leary et al. |
| 5,147,403 A | 9/1992 | Gitelis |
| 5,162,114 A | 11/1992 | Kuberasampath et al. |
| 5,219,897 A | 6/1993 | Murray |
| 5,236,456 A | 8/1993 | O'Leary et al. |
| 5,236,971 A | 8/1993 | Murray |
| 5,264,214 A | 11/1993 | Rhee et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,306,304 A | 4/1994 | Gendler |
| 5,314,476 A | 5/1994 | Prewett et al. |
| 5,320,844 A | 6/1994 | Liu |
| 5,336,699 A | 8/1994 | Cooke et al. |
| 5,356,629 A | 10/1994 | Sander et al. |
| 5,366,507 A | 11/1994 | Sottosanti |
| 5,385,887 A | 1/1995 | Yim et al. |
| 5,405,390 A | 4/1995 | O'Leary et al. |
| 5,417,975 A | 5/1995 | Lussi et al. |
| 5,425,769 A | 6/1995 | Snyders et al. |

(Continued)

FOREIGN PATENT DOCUMENTS

| | | |
|---|---|---|
| DE | 196 20 117 C1 | 7/1997 |
| GB | 2 093 348 A | 9/1982 |

(Continued)

OTHER PUBLICATIONS

Adkisson et al., "Rapid Quantitative bioassay of Osteoinduction", Journal of Orthopaedic Research, 18:503-511, 2000.

(Continued)

*Primary Examiner* — James Rogers
(74) *Attorney, Agent, or Firm* — Womble Carlyle Sandridge & Rice, LLP

(57) ABSTRACT

A composition includes calcium sulfate hemihydrate, stearic acid, an accelerant, and a mixing solution. The composition can be injected, e.g., through a needle, and is capable of setting, e.g., in vivo, in a relatively short period of time to a relatively high hardness.

20 Claims, No Drawings

(56) References Cited

U.S. PATENT DOCUMENTS

| | | |
|---|---|---|
| 5,439,684 A | 8/1995 | Prewett et al. |
| 5,462,722 A | 10/1995 | Liu et al. |
| 5,482,551 A | 1/1996 | Morris et al. |
| 5,484,601 A | 1/1996 | O'Leary et al. |
| 5,507,813 A | 4/1996 | Dowd et al. |
| 5,510,396 A | 4/1996 | Prewett et al. |
| 5,512,610 A | 4/1996 | Lin |
| 5,531,791 A | 7/1996 | Wolfinbarger, Jr. |
| 5,569,308 A | 10/1996 | Sottosanti |
| 5,573,771 A | 11/1996 | Geistich et al. |
| 5,578,662 A | 11/1996 | Bennett et al. |
| 5,614,206 A | 3/1997 | Randolph et al. |
| 5,618,549 A | 4/1997 | Patat et al. |
| 5,676,146 A | 10/1997 | Scarborough |
| 5,681,873 A | 10/1997 | Norton et al. |
| 5,697,981 A | 12/1997 | Ison et al. |
| 5,700,289 A | 12/1997 | Breitbart et al. |
| 5,707,962 A | 1/1998 | Chen et al. |
| 5,727,945 A | 3/1998 | Dannenbaum |
| 5,756,127 A | 5/1998 | Grisoni et al. |
| 5,763,416 A | 6/1998 | Bonadio et al. |
| 5,766,618 A | 6/1998 | Laurencin et al. |
| 5,769,897 A | 6/1998 | Harte |
| 5,788,976 A | 8/1998 | Bradford |
| 5,794,402 A | 8/1998 | Dumlao et al. |
| 5,807,567 A | 9/1998 | Randolph et al. |
| 5,824,087 A | 10/1998 | Aspden et al. |
| 5,830,493 A | 11/1998 | Yokota et al. |
| 5,861,445 A | 1/1999 | Xu et al. |
| 5,899,939 A | 5/1999 | Boyce et al. |
| 5,910,315 A | 6/1999 | Stevenson et al. |
| 5,948,426 A | 9/1999 | Jefferies |
| 5,948,428 A | 9/1999 | Lee et al. |
| 5,964,805 A | 10/1999 | Stone |
| 5,972,368 A | 10/1999 | McKay |
| 5,981,828 A | 11/1999 | Nelson et al. |
| 6,023,806 A | 2/2000 | Dumlao et al. |
| 6,030,635 A | 2/2000 | Gertzman et al. |
| 6,030,636 A | 2/2000 | Randolph et al. |
| 6,037,519 A | 3/2000 | McKay |
| 6,044,607 A | 4/2000 | Dumlao et al. |
| 6,051,247 A | 4/2000 | Hench et al. |
| 6,056,970 A | 5/2000 | Greenawalt et al. |
| 6,071,530 A | 6/2000 | Polson et al. |
| 6,083,522 A | 7/2000 | Chu et al. |
| 6,108,998 A | 8/2000 | Dumlao et al. |
| 6,118,043 A | 9/2000 | Nies et al. |
| 6,171,388 B1 | 1/2001 | Jobbins |
| 6,224,635 B1 | 5/2001 | Ricci et al. |
| 6,478,825 B1 | 11/2002 | Winterbottom et al. |
| 6,645,333 B2 | 11/2003 | Johnson et al. |
| 6,652,887 B1 | 11/2003 | Richelsoph et al. |
| 6,676,785 B2 | 1/2004 | Johnson et al. |
| 6,753,007 B2 | 6/2004 | Haggard et al. |
| 6,998,128 B2 | 2/2006 | Haggard et al. |
| 7,291,179 B2 | 11/2007 | Miller et al. |
| 7,371,408 B1 | 5/2008 | Petersen et al. |
| 7,371,409 B2 | 5/2008 | Petersen et al. |
| 7,371,410 B2 | 5/2008 | Petersen et al. |
| 7,658,768 B2 | 2/2010 | Miller et al. |
| 7,972,630 B2 | 7/2011 | Lidgren |
| 2002/0016636 A1 | 2/2002 | Ricci et al. |
| 2002/0071827 A1 | 6/2002 | Petersen et al. |
| 2003/0096718 A1 | 5/2003 | Sugimoto et al. |
| 2003/0143258 A1 | 7/2003 | Knaack et al. |

FOREIGN PATENT DOCUMENTS

| | | |
|---|---|---|
| WO | WO 89/04646 A1 | 6/1989 |
| WO | WO 96/39203 A1 | 12/1996 |
| WO | WO 98/40113 A1 | 9/1998 |
| WO | WO 99/15150 A1 | 4/1999 |
| WO | WO 0045734 A1 * | 8/2000 |
| WO | WO 00/74690 A1 | 12/2000 |
| WO | WO 0176649 A1 * | 10/2001 |
| WO | WO 02/05750 A2 | 1/2002 |
| WO | WO 03/024316 A2 | 3/2003 |
| WO | WO 03/030956 A2 | 4/2003 |
| WO | WO 03/045455 A1 | 6/2003 |

OTHER PUBLICATIONS

"Advances in Biomaterials for Bone Regeneration", Orthopedics, vol. 26, No. 5/Supplement, May 2003.

Betz, M.D., Randall R. "Limitations of Autograft and Allograft. New Synthetic Solutions", Orthopedics, vol. 25, No. 5, Supplement May 2002.

Biomaterials Tutorial, www.btec.cmu.edu/tutorial/biomaterials/biomaterials.htm, Undated.

"Bone Graft Substitutes Safe, Effective", AMA Science News Media Briefings, Dec. 6, 2001.

Greenwald et al., "Bone-Graft Substitutes: Facts, Fictions, and Applications", The Journal of Bone & Joint Surgery, JBJS Org., vol. 83-A, Supplement 2, Part 2, 2001.

Grimandi et al., "In vitro evaluation of a New Injectable Calcium Phosphate Material", J. Biomed. Mater Res., 1998, pp. 660-666, vol. 39, John Wiley & Sons, Inc.

Hanker et al., "Setting of Composite Hydroxylaptie/Plaster Implants with Blood for Bone Reconstruction", Proceedings of the 44th Annual Meeting of the Electron Microscopy Society of America, 1986.

Kelly, Ph.D., Evelyn B., "New Frontiers in Bone Grafting", Orthopaedic Technology Review, vol. 2, No. 9, Oct. 2000.

Turner et al.., "Radiographic and Histologic Assessment of Calcium o Sulfate in Experimental Animal Models and Clinical Use as a Resorbable Bone-Graft Substitute, a Bone-Graft Expander, and a Method for Local Antibiotic Delivery", The Journal of Bone and Joint Surgery, Incorporated, vol. 83-A, Supp. 2, Part 1, 2001.

* cited by examiner

BONE GRAFT SUBSTITUTE COMPOSITION

CROSS REFERENCE TO RELATED APPLICATIONS

This application is a continuation of U.S. application Ser. No. 11/739,416, filed on Apr. 24, 2007, which is a continuation of U.S. patent application Ser. No. 10/402,192, filed on Mar. 28, 2003, now U.S. Pat. No. 7,211,266, which claims priority under 35 U.S.C. §119(e) to U.S. Patent Application No. 60/368,924, filed on Mar. 29, 2002, the entire contents of which are hereby incorporated by reference.

TECHNICAL FIELD

The invention relates to bone graft substitute compositions.

BACKGROUND

Compositions containing calcium sulfate can be used as filler for voids or defects defined by bone. In some embodiments, the compositions can promote bone growth.

SUMMARY

The invention relates to bone graft substitute compositions. In one aspect, the invention features a composition including calcium sulfate, such as calcium sulfate hemihydrate, a binder, an accelerant, and a mixing solution.

In another aspect, the invention features a method including providing a mixture having calcium sulfate, such as calcium sulfate hemihydrate, a binder, and an accelerant, and contacting the mixture with a mixing solution.

Embodiments of the invention may include one or more of the following features. The calcium sulfate includes calcium sulfate hemihydrate. The binder includes stearic acid, hydroxypropylmethylcellulose (HPMC), hydroxymethylcellulose (HPC), and/or hyaluronic acid. The accelerant includes calcium sulfate dihydrate, and/or an ionic salt such as potassium sulfate or sodium sulfate. The mixing solution includes a saline solution.

Embodiments may have one or more of the following advantages. The composition is capable of setting or hardening in a relatively short time. In embodiments, the composition can harden to about 4 MPa in about 5-10 minutes. The composition is capable of setting or hardening in vivo. The composition can be injected through a needle, e.g., an 11-13 gauge needle up to about 10 cm long.

Other features and advantages of the invention will be apparent from the description of the preferred embodiments thereof and from the claims.

DETAILED DESCRIPTION

A bone graft substitute composition includes calcium sulfate, such as calcium sulfate hemihydrate ($CaSO_4 \cdot \frac{1}{2}H_2O$), a binder, such as stearic acid, a material that accelerates hardening of the composition ("an accelerant"), and a mixing solution. In some embodiments, the calcium sulfate, the binder, and the accelerant are provided as a mixture of powders to which the mixing solution is added to form the composition. The composition can be delivered to a target site by injecting the composition through a needle. The composition can harden in vivo, e.g., such that the hardened composition is capable of supporting orthopedic hardware.

The calcium sulfate is preferably calcium sulfate hemihydrate, $CaSO_4 \cdot \frac{1}{2}H_2O$. Without wishing to be bound by theory, it is believed that during use, e.g., after mixing the powder mixture with the mixing solution, the calcium sulfate hemihydrate is converted, e.g., changes crystalline form, into calcium sulfate dihydrate ($CaSO_4 \cdot 2H_2O$), which hardens the composition. Calcium sulfate dihydrate is capable of being sorbed by the body. In some embodiments, the mixture of powders includes greater than about 90 weight percent of calcium sulfate, e.g., calcium sulfate hemihydrate. The mixture may include greater than 90, 91, 92, 93, 94, 95, 96, 97, 98, or 99 weight percent of calcium sulfate hemihydrate; and/or less than 100, 99, 98, 97, 96, 95, 94, 93, 92, or 91 weight percent of calcium sulfate hemihydrate. Methods of making a calcium sulfate hemihydrate is described in U.S. Pat. Nos. 5,614,206; 5,807,567; and 6,030,636, all hereby incorporated by reference in their entirety.

Without wishing to be bound by theory, it is believed that the binder provides the composition with a consistency that helps the composition to flow, e.g., to be injectable. It is believed that, for example, stearic acid may also make the composition relatively hydrophobic, for example, which may lubricate the inner wall of a syringe and enhance flow of the composition. In some embodiments, the mixture of powders includes between about 1 and 2, e.g., about 1.5-2.0, weight percent of the binder. The mixture may include greater than 1.0, 1.1, 1.2, 1.3, 1.4, 1.5, 1.6, 1.7, 1.8, or 1.9 weight percent of the binder; and/or less than 2.0, 1.9, 1.8, 1.7, 1.6, 1.5, 1.4, 1.3, 1.2, or 1.1 weight percent of the binder. Examples of binders include stearic acid, hydroxypropylmethylcellulose (HPMC), hydroxymethylcellulose (HPC), and hyaluronic acid. Mixtures of two or more binders may be used.

Without wishing to be bound by theory, the accelerant is believed to enhance, e.g., accelerate, the conversion of calcium sulfate hemihydrate to calcium sulfate dihydrate. In particular, it is believed that particles of the accelerant act as crystallization nucleation sites for the conversion of calcium sulfate hemihydrate to calcium sulfate dihydrate. Examples of accelerants include calcium sulfate dihydrate, potassium sulfate, or sodium sulfate. Other examples include ionic salts. A preferred accelerant is calcium sulfate dihydrate crystals (available from U.S. Gypsum) coated with sucrose (available from VWR Scientific Products). A process of stabilizing the dihydrate crystals by coating with sucrose is described in U.S. Pat. No. 3,573,947, hereby incorporated by reference in its entirety. In some embodiments, the mixture of powders includes between about 0.1 and 0.5 weight percent of the accelerant. The mixture may include greater than 0.10, 0.15, 0.20, 0.25, 0.30, 0.35, 0.40, or 0.45 weight percent of the accelerant; and/or less than 0.50, 0.45, 0.40, 0.35, 0.30, 0.25, 0.20, or 0.15 weight percent of the accelerant. Mixtures of two or more accelerants can be used.

The mixing solution is generally selected to provide the composition with a desired consistency and hardening time. Examples of a mixing solution include water, e.g., sterile water, solutions containing inorganic salts, or cationic surface-active agents including sodium chloride, saline, e.g., phosphate buffered saline, potassium chloride, sodium sulfate, potassium sulfate, EDTA, ammonium sulfate, ammonium acetate, and sodium acetate. A specific example of a mixing solution is 0.9% NaCl saline solution (available from Baxter). In some embodiments, for a 25 g mixture of powders, preferably about 8-10 cc of mixing solution is added to the mixture to form a composition. Mixtures of two or more mixing solutions can be used.

The mixing solution can further include, for example, bone marrow aspirate, platelet concentrate, blood, pharmaceutical additives in solution, or combinations of these materials. Examples of additives are medicaments or pesticides.

Examples of medicaments are antibiotics, chemotherapeutic agents, growth factors, and analgesics. Examples of antibiotics are tetracycline hydrochloride, vancomycin, cephalosporins, and aminoglycocides such as tobramycin and gentamicin. Examples of chemotherapeutic agents are cis-platinum, ifosfamide, methotrexate, and doxorubicin hydrochloride (Adriamycin®). Examples of growth factors are transforming growth factor beta (TGF-Beta), bone morphogenic protein (BMP), basic fiberblast growth factor, platelet-derived growth factor, and other polypeptide growth factors. Examples of analgesics are anesthetics such as lidocaine hydrochloride (Xylocaine®), bipivacaine hydrochloride (Marcaine®), and non-steroidal anti-inflammatory drugs such as ketorolac tromethamine (Toradol®). Certain mixing solutions can affect, e.g., delay, the hardening properties of the composition.

The composition can be formed by providing the mixture of powders (e.g., calcium sulfate hemihydrate, stearic acid, and calcium sulfate dihydrate) and contacting, e.g., mixing, the mixture with a mixing solution (e.g., NaCl saline) to form the composition. The composition may be a conforming material having a paste-like consistency, e.g., like Plaster of Paris. The material can be injected into a target site, for example, to fill into cracks or voids. In some embodiments, the material can be injected through an 11 to 13-gauge needle up to, for example, 10 cm long. The material is capable of setting to a hardness comparable to or greater than bone within about 5-10 minutes, e.g., greater than 5, 6, 7, 8, or 9 minutes, and/or less than 10, 9, 8, 7, or 6 minutes. The material can have a Vicat set time of about 5-10 minutes, e.g., 5-6 minutes. The material is capable of hardening to about >4 MPa.

The hardened composition can be used for intra-operative support of hardware, such as orthopedic hardware, e.g., bone plates, distal radius hardware, and hardware used for tibial plateau fractures.

Other Embodiments

In some embodiments, the composition further includes a bioactive agent. Examples of bioactive agents include demineralized bone matrix, growth factors, hyaluronic acid, bone morphogenic proteins, bone autograft, and bone marrow, etc. The composition may include sodium bicarbonate. For example, the composition may include 0.1-2% sodium bicarbonate by weight to provide a porous structure in the resultant composition.

Alternatively or in addition, the bone graft substitute composition may include one or more additives such as an antiviral agent, an antimicrobial agent, an antibiotic agent, an amino acid, a peptide, a vitamin, an inorganic element, a protein synthesis co-factor, a hormone, an endocrine tissue, a synthesizer, an enzyme, a polymer cell scaffolding agent with parenchymal cells, an angiogenic drug, demineralized bone powder, a collagen lattice, an antigenic agent, a cytoskeletal agent, mesenchymal stem cells, a bone digester, an antitumor agent, a cellular attractant, fibronectin, a growth hormone, a cellular attachment agent, an immunosuppressant, a nucleic acid, a surface active agent, calcium phosphate materials, such as hydroxyapatite or tricalcium phosphate, a penetration enhancer, a bone allograft, cancellous bone chips (an osteoconductive substrate), and chunks, shards, and/or pellets of calcium sulfate.

The bone graft substitute composition can also be used as a carrier, for example, by mixing it with other materials, such as, for example, allografts, antibiotics, growth factors, cancellous bone chips, or synthetically derived or naturally derived chips of minerals such as calcium phosphate or calcium carbonate. This can provide the composition with versatility and flexibility by allowing a user to formulate a mixed composition according to a desired application.

The following example is illustrative and not intended to be limiting.

EXAMPLE

A 25-gram mixture of powders was formed having 98.08 wt % of $CaSO_4 \cdot \frac{1}{2}H_2O$, 1.77 wt % of stearic acid (triple pressed powder, available from VWR Scientific Products), and 0.15 wt % of $CaSO_4 \cdot 2H_2O$. About 9 cc of mixing solution (0.9% NaCl saline) was added to the mixture of powders, and mixed together to form a composition having a paste-like consistency.

The composition could be injected through a 6 cm long, 11-gauge needle. After about 7 minutes, the composition hardened, e.g., comparable to the hardness of bone. More specifically, the composition hardened to about 8 MPa (8.17 MPa±0.23, n=3) after after about twenty minutes; to about 17 MPa (16.54 MPa±1.05, n=8) after about one hour; and to about 35 MPa (34.94 MPa±4.04, n=5) after about 24 hours.

As described above, the composition can also harden in vivo. Following procedures similar to ASTM-F451, cylindrical samples (6 mm diameter, 12 mm high) of the composition were submerged in bovine calf serum to simulate in vivo conditions. The hardness of the samples was measured at different times. After about seven minutes, the composition hardened to about 1 MPa (1.04 MPa±0.29, n=3). After about twenty minutes, the composition hardened to about 4 MPa (3.82 MPa±0.87, n=3). After about one hour, the composition hardened to about 15 MPa (14.94 MPa±0.82, n=8). After about 24 hours, the composition hardened to about 10 MPa (10.59±0.73, n=8).

The amount of mixing solution added to the mixture of powders can affect the time the composition takes to set, i.e., the set time. Increasing the amount of mixing solution can increase the set time. For example, in embodiments, adding more than 12 cc of saline to the above 25-gram mixture may delay hardening to over 30-40 minutes. Decreasing the amount of mixing solution added to the mixture of powders can reduce the set time, but injecting the composition can be relatively difficult. Other embodiments are within the claims.

What is claimed is:

1. A bone graft substitute composition kit, comprising: a powder mixture comprising greater than about 90 weight percent calcium sulfate hemihydrate, an accelerant for accelerating conversion of calcium sulfate hemihydrate to calcium sulfate dihydrate, the accelerant present in an amount of less than about 0.5 percent by weight of the powder mixture, and stearic acid in an amount of at least about 1.0 percent by weight of the powder mixture; an aqueous mixing solution; and an additional component selected from the group consisting of antiviral agents, antimicrobial agents, antibiotic agents, surface-active agents, antitumor agents, demineralized bone matrix, mesenchymal stem cells, bone marrow, growth factors, calcium phosphate materials, sodium bicarbonate, bone allograft, cancellous bone chips, pellets of calcium sulfate, and mixtures thereof.

2. The bone graft substitute composition kit of claim 1, wherein the powder mixture comprises greater than about 95 weight percent calcium sulfate hemihydrate.

3. The bone graft substitute composition kit of claim 1, wherein the aqueous mixing solution is a saline solution.

4. The bone graft substitute composition kit of claim 1, wherein the aqueous mixing solution comprises at least one inorganic salt or at least one cationic surface-active agent.

5. The bone graft substitute composition kit of claim 1, wherein the powder mixture comprises about 0.1 to about 0.5 weight percent of said accelerant.

6. The bone graft substitute composition kit of claim 1, wherein the powder mixture comprises about 1.0 to about 2.0 weight percent of stearic acid.

7. The bone graft substitute composition kit of claim 1, wherein the bone graft substitute composition produced by mixing said powder mixture and said aqueous mixing solution has a Vicat set time of about 5 to about 10 minutes.

8. The bone graft substitute composition kit of claim 1, wherein the accelerant is present in an amount of about 0.1 to about 0.5 weight percent, and the stearic acid is present in an amount of about 1.0 to about 2.0 weight percent.

9. The bone graft substitute composition kit of claim 1, wherein the accelerant is present in an amount of less than about 0.3 percent by weight of the powder mixture, and stearic acid in an amount of at least about 1.5 percent by weight of the powder mixture.

10. The bone graft substitute composition kit of claim 1, wherein the accelerant is selected from calcium sulfate dihydrate and calcium sulfate dihydrate coated with sucrose.

11. The bone graft substitute composition kit of claim 1, wherein the accelerant is calcium sulfate dihydrate coated with sucrose.

12. The bone graft substitute composition kit of claim 1, wherein the bone graft substitute composition produced by mixing said powder mixture and said aqueous mixing solution is injectable through a needle.

13. The bone graft substitute composition kit of claim 1, wherein the bone graft substitute composition kit further comprises sodium bicarbonate and the bone graft substitute composition produced by mixing said powder mixture and said aqueous mixing solution has a porous structure.

14. The bone graft substitute composition kit of claim 1, wherein the additional component comprises demineralized bone matrix.

15. The bone graft substitute composition kit of claim 1, wherein the additional component comprises an antibiotic agent.

16. The bone graft substitute composition kit of claim 15, wherein the antibiotic is selected from the group consisting of tetracycline hydrochloride, vancomycin, cephalosporins, tobramycin, and gentamicin.

17. The bone graft substitute composition kit of claim 1, wherein the additional component comprises a growth factor.

18. The bone graft substitute composition kit of claim 17, wherein the growth factor is selected from the group transforming growth factor beta, bone morphogenic protein, basic fiberblast growth factor, and platelet-derived growth factor.

19. The bone graft substitute composition kit of claim 1, wherein the additional component comprises an antitumor agent.

20. The bone graft substitute composition kit of claim 1, wherein the additional component comprises a calcium phosphate material.

* * * * *